US007520419B2

(12) United States Patent
Libin et al.

(10) Patent No.: US 7,520,419 B2
(45) Date of Patent: Apr. 21, 2009

(54) METHOD FOR TRANSMITTING MEDICAL INFORMATION IDENTIFIED BY A UNIQUE IDENTIFIER

(75) Inventors: Barry Libin, Great Neck, NY (US); Aaron Wachspress, Great Neck, NY (US)

(73) Assignee: BML Medrecordsalert LLC, Great Neck, NY (US)

( * ) Notice: Subject to any disclaimer, the term of this patent is extended or adjusted under 35 U.S.C. 154(b) by 152 days.

(21) Appl. No.: 11/643,241

(22) Filed: Dec. 21, 2006

(65) Prior Publication Data
US 2007/0138253 A1  Jun. 21, 2007

Related U.S. Application Data

(60) Provisional application No. 60/752,624, filed on Dec. 21, 2005.

(51) Int. Cl.
*G06K 17/00* (2006.01)
*G06Q 50/00* (2006.01)
*A61B 5/00* (2006.01)
*G06F 19/00* (2006.01)

(52) U.S. Cl. ........................... 235/375; 235/487; 705/2; 705/3

(58) Field of Classification Search ................ 235/375, 235/487; 705/2, 3
See application file for complete search history.

(56) References Cited

U.S. PATENT DOCUMENTS 7,251,609 B1 * 7/2007 McAlindon et al. ............ 705/3

| | | |
|---|---|---|
| 2002/0016750 A1 | 2/2002 | Attia |
| 2002/0111830 A1 * | 8/2002 | Tahan ............................. 705/3 |
| 2003/0074328 A1 * | 4/2003 | Schiff et al. ................... 705/75 |
| 2004/0054935 A1 * | 3/2004 | Holvey et al. ............... 713/202 |
| 2004/0153344 A1 * | 8/2004 | Bui et al. ......................... 705/3 |
| 2004/0210458 A1 * | 10/2004 | Evans et al. .................... 705/2 |
| 2005/0004844 A1 | 1/2005 | Attia |
| 2005/0011957 A1 | 1/2005 | Attia et al. |
| 2005/0015310 A1 | 1/2005 | Frantz et al. |
| 2005/0015311 A1 | 1/2005 | Frantz et al. |
| 2005/0029354 A1 | 2/2005 | Frantz et al. |

(Continued)

FOREIGN PATENT DOCUMENTS

WO      WO2005/017812      2/2005

(Continued)

*Primary Examiner*—Thien M. Le
*Assistant Examiner*—Tuyen K Vo
(74) *Attorney, Agent, or Firm*—James V. Costigan; Hedman & Costigan, P.C.

(57) ABSTRACT

A method for transmitting personal health information from a databank to a health facility. An individual's health information is stored in a database, and the information is sent to authorized users as needed. The information is stored in the database by coding an individual's private file with a unique identifying number or alpha-numeric sequence. The individual is provided with an electronically readable identifier (ERI) that corresponds to the unique identifying number or alpha-numeric sequence. The ERI can be scanned by medical personnel with the appropriate scanner. The scanner is authenticated by the database, and the information corresponding to that individual is sent back to the scanner for use by the emergency medical personnel. The health information can also be sent to a hospital. The entire process requires authentication of the medical personnel and validation of the ERI for security purposes.

24 Claims, 3 Drawing Sheets

U.S. PATENT DOCUMENTS

| | | |
|---|---|---|
| 2005/0029356 A1 | 2/2005 | Frantz et al. |
| 2005/0033599 A1 | 2/2005 | Frantz et al. |
| 2005/0035206 A1 | 2/2005 | Attia et al. |
| 2005/0082370 A1 | 4/2005 | Frantz et al. |
| 2005/0246196 A1 | 11/2005 | Frantz et al. |
| 2006/0106646 A1* | 5/2006 | Squilla et al. ................... 705/3 |
| 2006/0255143 A1* | 11/2006 | Ehrhart ....................... 235/454 |

FOREIGN PATENT DOCUMENTS

| | | |
|---|---|---|
| WO | WO2005/020140 | 3/2005 |

* cited by examiner

METHOD FOR TRANSMITTING MEDICAL INFORMATION IDENTIFIED BY A UNIQUE IDENTIFIER

CROSS REFERENCE TO RELATED APPLICATIONS

The present application claims priority from provisional patent application Ser. No. 60/752,624 filed on Dec. 21, 2005

FIELD OF THE INVENTION

The invention relates to transmitting patient health information stored at a central databank to a hospital and particularly to identifying which health information to send via the use of an electronically readable identifier (ERI) and a scanner.

BACKGROUND OF THE INVENTION

Mobile devices for scanning barcodes or other electronically readable identifiers (ERI) are well known. Additionally, methods exist for enhancing barcodes that are scanned into mobile devices. Further, it has been taught how to use scanned barcodes to facilitate online shopping. However, scanners in the prior art do not provide security to users to prevent information being delivered to the wrong hands. Additionally, the prior art does not teach the use of such methods for transmitting health information to emergency medical personnel or how individuals can input information to create their own personal medical database, which may be retrieved using portable scanning technology.

For example, United States Patent Application Publication 2005/0246196 by Frantz et al. teaches the use of cell phones or other mobile devices only to scan barcodes of purchased products. The user then answers questions related to the purchased product, and the answers are stored in a user database which is used to track consumer patterns and trends.

United States Patent Application Publication 2005/0082370, also by Frantz et al., is limited to methods for enhancing a barcode that is scanned with a mobile device. After being scanned, the barcode is sent as an image to a server which enhances the image and proceeds to decode the information contained in the barcode. The information is decoded and media content related to the barcode is sent back to the mobile device.

United States Patent Application Publication 2005/0015311, also by Frantz et al., teaches the use of a mobile device to scan barcodes of products desired to be purchased. The device is then attached to a computer which uploads the information contained in the scanned barcodes to various vendors based upon predetermined preferences. The computer then launches a browser with a populated shopping cart at each vendor's e-commerce website, thus allowing a user to pick-and-choose from among items.

WO 2005/020140 and United States Patent Application Publication 2005/0035206, both by Attia et al., disclose a system and method for enhancing images of barcodes taken by the digital camera connected to a mobile device. The system involves converting an image into gray scale and using an algorithm to compute the mean pixel intensity value of each row of pixels in the image. Using these values, the algorithm is able to reconstruct the barcode as an enhanced image.

WO 2005/017812 and United States Patent Application Publication 2005/0011957, both by Attia et al., teach the use of a mobile device to take a digital picture of a barcode. Software on the mobile device then enhances the barcode and subsequently decodes the barcode. The information is then transmitted to a server via a wireless network, and the server then transmits media content related to the information back to the mobile device.

United States Patent Application Publication 2005/0004844 by Attia discloses a system and method for easily and rapidly integrating barcode scanner-enabled products and services into existing e-commerce application-providers, thus upgrading the existing websites. Attia accomplishes this through use of floating pop-up web windows which take the user away from a dealer's website.

United States Patent Application Publication 2002/0016750 by Attia discloses a method for shoppers to scan barcodes of desired products and to eventually store these barcodes on a website for later retrieval.

United States Patent Application Publication 2005/0033599 to Frantz et al. discloses a method for creating catalogs for ordering supplies. A unique catalog can be created for individual users by selecting a desired list of products from a pre-existing list using a software application on a computer. The user then selects the layout of the document from several predefined layouts. The catalog is created, and since it is unique to the user, it can be reused.

United States Patent Application Publication 2005/0029356 to Frantz et al. discloses a way to transfer data from barcode scanners to computers. An Active-X plug-in is downloaded to the user's computer the first time an application is accessed. The Active-X plug-in aids the transfer and translation of data from the user's barcode scanner to the computer.

United States Patent Application Publication 2005/0029354 to Frantz et al. discloses a method of encoding and decoding a barcode which contains a combination barcode.

United States Patent Application Publication 2005/0015310 to Frantz et al. discloses a system and method for managing client orders from multiple vendors utilizing barcode scanning technology. Client identification barcodes are utilized to identify each of the user's clients. To order products for a client, a user first scans the client identification barcode using a barcode scanner and then scans the barcodes of the desired products. This process can be repeated for multiple clients. A software program is then utilized to upload the barcode information, create shopping lists, and upload the information to different vendor websites for order completion

SUMMARY OF THE INVENTION

In order to store the individual's medical information in a database, information is entered (either by the individual or other authorized user) into a private file. The private file is coded with a unique identifying number or alpha-numeric sequence, and an electronically readable identifier (ERI) is generated which corresponds to the unique identifying number or alpha-numeric sequence. The individual will keep a document with a copy of this ERI in a convenient location, e.g., on the refrigerator, in a car, imprinted on a necklace, in a wallet, or as a tattoo.

When a medical emergency occurs, and emergency medical personnel arrive on scene, the medical personnel will scan the ERI with a mobile device, such as a cell phone or PDA, which is equipped with a scanner. The ERI is wirelessly transmitted to the database. Along with the ERI, the mobile device also transmits its own unique reference number or alpha-numeric sequence, e.g., its phone number, serial number, EMI or MAC (media access control) address. In the database, the ERI is matched with the private file to which it corresponds and is then validated, and the unique reference number or alpha-numeric sequence is matched against a list of pre-approved reference numbers or alpha-numeric sequences and is then authenticated. If the unique identifying number or alpha-numeric sequence is validated, the mobile device is authenticated, and a private password entered, then the medical information contained in the private file is wirelessly transmitted back to the mobile device, so that the emergency medical personnel have the patient's vital information at their fingertips. The information can also be sent by fax or via hyper text transport protocol secure (HTTPS) to a client software package from the database to a hospital or other health facility if the emergency medical personnel indicates on the mobile device that the patient is going to a hospital or other health facility. The mobile device will display a list of hospitals and other health care facilities served by the emergency medical personnel based upon information gathered when the mobile device was registered to the database. The ERI may comprise a printed barcode or a radio frequency identification device (RFID).

From time to time, it may become necessary to update the stored healthcare information, such as with new test results and updated advance directives. Local regulations require that certain advance directives be updated regularly and therefore the web site will send out periodic emails to remind the individual to update these documents, The individual can accomplish this by logging into a specified website and accessing his or her private file. The individual can choose from several types of information to input, e.g., new test results, advance directives such as DNRs, etc. New test results are documents which the individual generally has in hand if received from his/her physician. Advance directives are documents which are generally printed from the web site then signed and witnessed. The individual begins the process of storing these documents in his/her private file by selecting the option to fax the information to the file. This causes a cover sheet including a bar code corresponding to a unique confirmation number or alpha numeric sequence to be printed out. The unique identifying number or alpha-numeric sequence is used to identify the individual and the type of document being faxed. The individual may then deliver the cover sheet and the documents by fax to a provided number, which will then cause the information (e.g., the cover sheet and the document) to be scanned into a blank file in the private file. The unique confirmation number read from the corresponding bar code located on the fax cover sheet is matched with the blank file in the private file, and the contents of the fax are loaded into the blank file. The blank file is then locked. The individual must then log on to the website and review the information that is in the locked file. If the information is satisfactory, the user can unlock the file and the information will then be transmitted when requested by emergency medical personnel. If the information is not satisfactory, the individual has the option of deleting the blank file and starting from the beginning. With regard to certain types of information, e.g., laboratory test results, these may be transmitted electronically using appropriate codes to insure confidentiality.

Documents may be uploaded to the private file via HTTPS connection using a document scanning device. Images of documents may also be uploaded via HTTPS connection. Documents added to the private file in this manner are also locked until the individual logs onto the web site to review and approve the documents.

In order to increase security of the system, the unique identifying number or alpha-numeric sequence associated with the ERI, the unique confirmation number or alpha-numeric sequence associated with the private file, and the unique reference number or alpha-numeric sequence associated with the mobile device can all be generated with suitable algorithm software. In order to create a unique alpha-numeric sequence which is independent from any previously generated alpha-numeric sequence, the algorithm randomly selects a combination of thirty-two letters and Arabic numerals. Next, the algorithm retrieves from the web server's operating system a GUID (global unique identifier) which is added to the previously generated succession to create an array. Third, the array is shifted bit by bit several times. Fourth, a hex number is added to the array to create a string. Two of these strings are added together, and the first twelve symbols are used as the unique alpha-numeric sequence.

The medical information can be sent to places other than emergency medical personnel and hospitals. For example, other facilities that would find a use for this invention include a doctor's office, an emergency room, a nursing home, a convalescence home, an infirmary, a hospice or other health care facility.

Additionally, many different types of encoding ERIs are known. It is contemplated that this invention will work with any of the currently known ERIs or any as yet undeveloped ERIs. Currently known barcodes with which this invention will work include UPC-A, UPC-E, ISBN, RSS-14, RSS-14E, RSS-14L, Interleaved 2 of 5, EAN/JAN-8, EAN/JAN-13, Code 3, Code 39 Full ASCII, Code 128, PDF417, QR Code, and Data Matrix.

Furthermore, it is contemplated that various types of medical information will be transmitted to health facilities and to mobile devices as needed. The types of medical information contemplated include, but are not limited to, medical history, surgical history, recent lab/test results, imaging studies, blood type, immunization history, medical device information, family history, social history, allergies, advanced directives such as DNRs, living wills, durable power of attorney, genetic information, medical power(s) of attorney, next-of-kin contact information, current medications, current supplements, current vitamins, drug tests, name and contact information for current physicians, choices of hospital and digital photograph.

Further modifications of this invention are also possible. One modification is that a computer is used in place of a scanner. The Internet public IP address of the computer would function as the unique reference number or alpha-numeric sequence. Additionally, it is foreseen that, once information has been transmitted to emergency medical personnel or other health care facility, the system would automatically contact a list of people previously supplied by the individual, such as next-of-kin. This automatic contact could be in the form of email, instant message, or synthesized voice over, for example, a telephone. It is further foreseen that the system can send periodic reminders to the individual to remind them to update stored medical and healthcare information as necessary.

It is also envisioned that an individual's entire medical information that is already stored can be copied to a portable device such as a USB flash memory device or memory card. The device or card can be attached to a keychain, imbedded in a wrist band or stored as a credit card format. Medical personnel would then be able to access the medical information immediately, without having to resort to scanning and transmitting ERIs, and awaiting return communications. The individual could either require a password to access the information or leave it in an unsecured format. The device or card could be read by any of a number of instruments including, but not limited to, a desktop or laptop computer, an electronic personal organizer, and a cellular phone. The device or card could be updated with new medical information by connecting it to the internet, accessing the specified website, logging into one's personal file, and downloading any new information into the device or card.

It is therefore an object of the present invention to efficiently transmit patient identifying information to a central database in order for emergency medical personnel to obtain a patient's medical history. It is a further object of the present invention to keep such transmissions secure from unauthorized individuals. It is an even further object of the present invention to allow a patient to update medical information from the comfort and privacy of the patient's home. Another object of the present invention is to allow emergency medical personnel to utilize this invention without the need for expensive proprietary equipment. Yet another object of this invention is to allow a hospital to obtain medical information while a patient is en route to the hospital.

The present invention achieves these and other objectives wherein it is directed to a method for transmitting personal health information from a database to a health facility. The transmission involves initially storing an individual's medical information in a database and allowing the stored information to be retrieved by an authorized user using a valid ERI which identifies the individual.

BRIEF DESCRIPTION OF THE DRAWINGS

The attached drawing figures, in which like reference characters represent like steps, are included solely to illustrate the preferred embodiment of the present invention without limiting the invention in any manner whatsoever, wherein.

DETAILED DESCRIPTION OF THE PRESENT INVENTION

Figure 1:
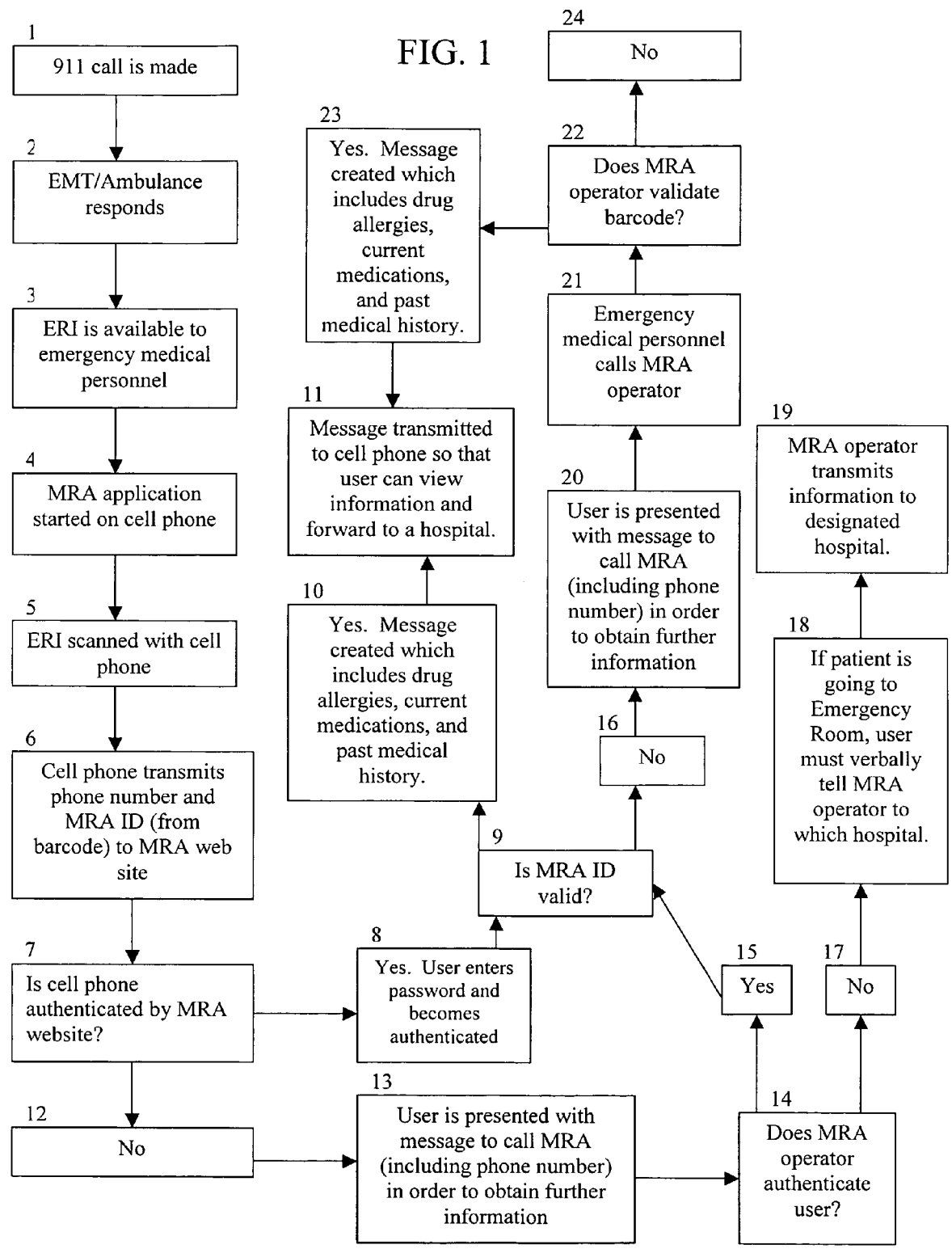
FIG. 1 is a flowchart of the steps taken once an emergency is discovered.

As best shown in FIG. 1, once an emergency 911 call is made (1), and an ambulance (or other emergency medical personnel) responds (2), the invention is deployed. Initially, a patient identifier is provided which is used to retrieve a patient's medical history. This may be done from a manual directory or a computer algorithm, such as described above. A card or other record containing a unique ERI may be provided for a patient to make available to emergency medical personnel (3). The record can be carried around by the patient on a necklace, on a bracelet, in a wallet, or stored in a convenient location in one's home or car. Once the card is found, the medical personnel activate the software application that is already loaded onto a cell phone (4). An example of this software is Scanzoom available from Scanbuy, 54 W. 39$^{th}$ Street, New York, N.Y. 10018. The medical personnel may use a cell phone to scan the ERI (5). The cell phone transmits its own phone number and the ERI to a central database (6). The database then matches the phone number to a list of pre-approved phone numbers (7). If the cell phone is authenticated and the user furnishes the appropriate password (8), then the database will compare the alpha-numeric sequence to a list of stored ERIs (9). If the ERI is validated, the database creates a message containing the patient's medical information, including drug allergies, current medications, and past medical history (10). This message is then transmitted back to the cell phone so the emergency medical personnel will be informed of the medical history (11).

If, during cell phone authentication (7), the cell phone is not authenticated (12), then the user is presented with a message on the cell phone to call a specified number for a customer service representative in order to obtain further information (13). The emergency medical personnel will then need to call the customer service representative in order to have the cell phone authenticated (14). If the customer service representative authenticates the cell phone (15), then the ERI will be compared to a list of ERIs stored in the database (9). If the ERI is validated, the database creates a message containing the patient's medical information, including drug allergies, current medications, and past medical history (10). This message is then transmitted back to the cell phone so the emergency medical personnel will be informed of the medical history (11).

If at any time after the cell phone is authenticated (8), the ERI corresponding to the barcode is not validated (16), the cell phone user is presented with a message to call a specified number for a customer service representative in order to obtain further information (20). The emergency medical personnel will then need to call the customer service representative in order to have the ERI (21). The customer service representative will then validate the ERI by comparing it to a list of ERIs stored in the database (22). If the ERI is validated, the database creates a message containing the patient's medical information, including drug allergies, current medications, and past medical history (23). This message is then transmitted back to the cell phone so the emergency medical personnel can access the information (11).

If, during manual authentication of the cell phone number (14), the cell phone number is not authenticated (17), the medical personnel must verbally request that the customer service representative transmit the medical information to a hospital (18). The customer service representative then transmits the medical information to the designated hospital (19).

If, during manual validation of the ERI (22), the ERI is not validated by the customer service representative (24), then no transmission is made to a hospital and the emergency medical personnel will proceed with the traditional procedures involving ambulances and hospitals.

Figure 2:
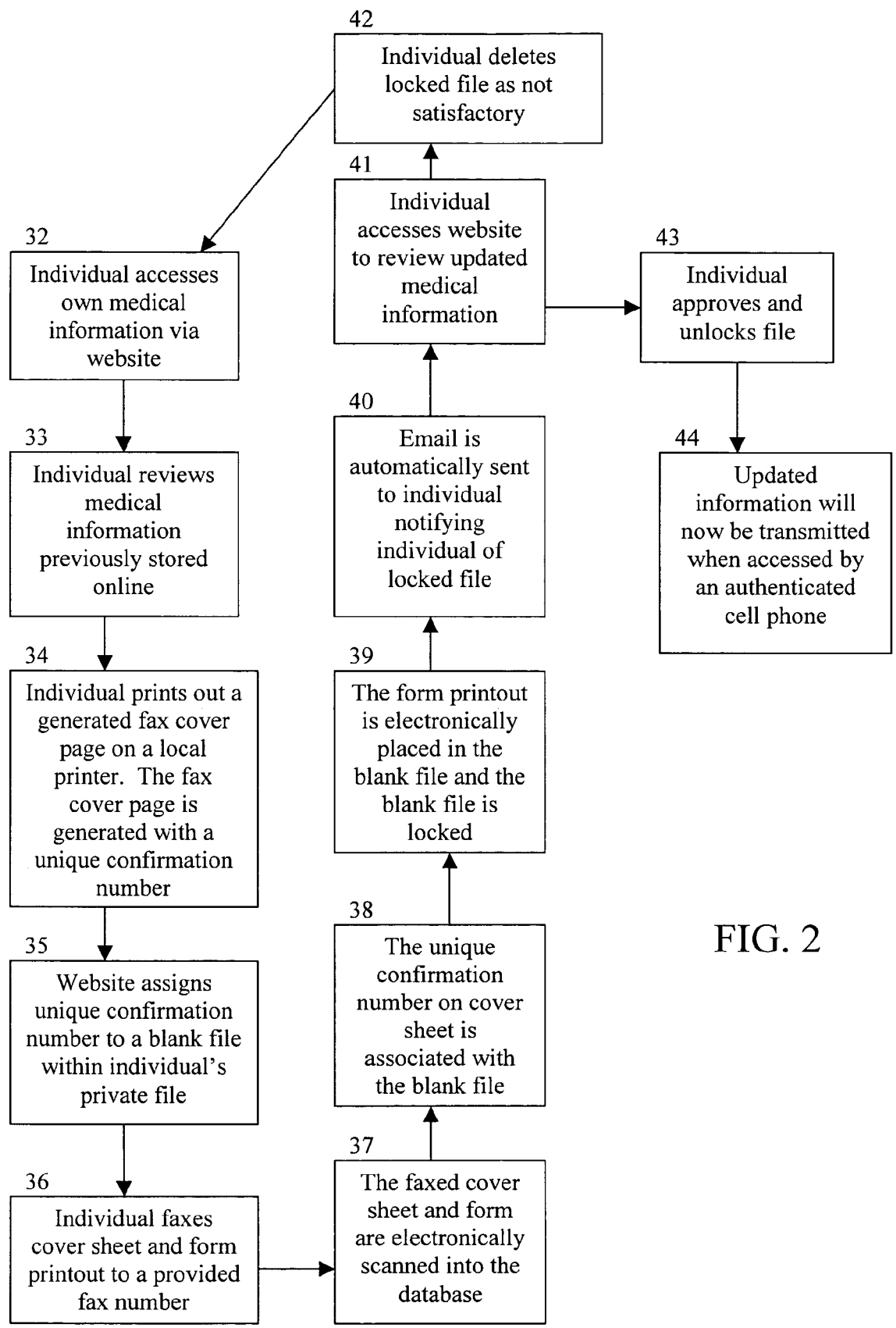
FIG. 2 is a flowchart of the steps taken to input and update medical information contained in the database.

As best shown in FIG. 2, in order to update medical information contained in the database via facsimile, an individual must first logon to the website (32). The individual can then review information previously stored online in the database (33). The individual updates medical information via facsimile by first printing out a fax cover page on a local printer which is generated with a unique confirmation number (34). The website assigns the unique confirmation number to a blank file within the individual's private file (35). The individual then faxes the cover sheet and form printout (containing the updated medical information) to a provided fax number (36). The faxed cover sheet and form printout are electronically scanned into the database (37). The unique confirmation number on the cover sheet (which has now been scanned into the database) is read by the database and associated with the blank file (38). The form printout is electronically placed into the blank file and the file is locked (39). An automatically generated email is then sent to an email address the individual has previously provided in order to notify the individual that the fax has been received, scanned, and locked (40). The individual then must access the website in order to review the medical information stored in the locked file (41). If the information is not satisfactory to the individual, the individual can delete the locked file (42). The individual may then proceed to accessing (31) and updating medical information again (32).

If, after accessing and reviewing the healthcare information stored in the locked file (41), the individual decides the information is proper, the individual approves and unlocks the information (43). The information is now updated and will be transmitted when accessed by an authenticated cell phone or any other device used to access the web site. (44).

Figure 3:
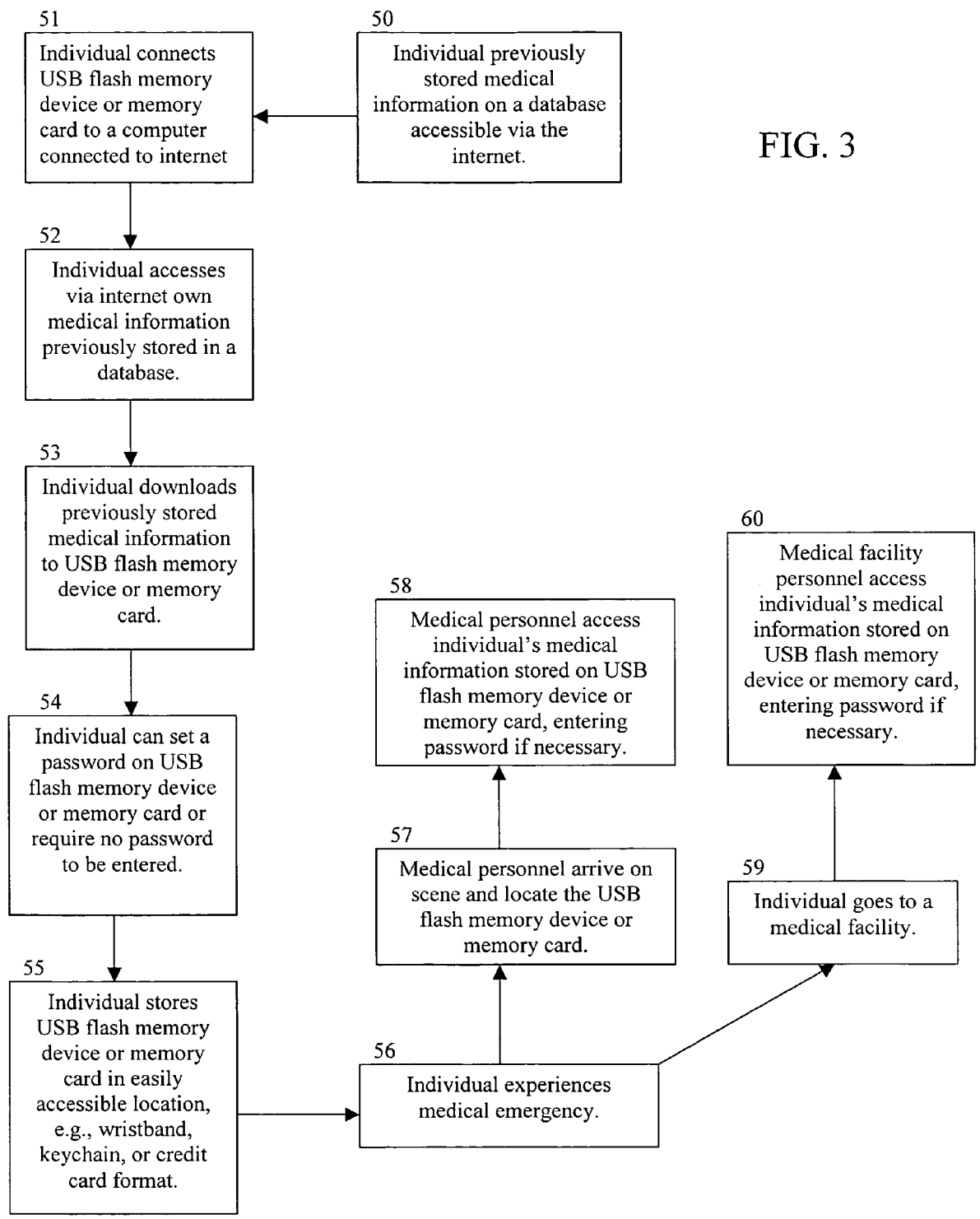
FIG. 3 is a flowchart of the steps taken to allow an individual to carry around medical information in a portable device such as a USB flash memory device or memory card.

As best shown in FIG. 3, the individual can carry medical information in a portable device. The individual would first have to have previously placed personal medical information into a file stored on a database that is accessible via the internet (50). The individual would then be able to connect the portable device, preferably a USB flash memory device or other memory card, to a computer that is connected to the internet (51). Next, the individual would access medical information previously saved on a database (52). It is envisioned that step (51) can be completed immediately before step (52) (as shown), or step (51) can be completed immediately after step (52) (not shown). Once the personal medical information is accessed and the portable device is connected to the computer, the individual can then download all the medical information to the device (53). The individual can then either set a password to require access to the medical information stored on the portable device or leave the information in an unsecured format (54). Once the portable device is disconnected from the computer (not shown), the individual can store the portable device in an easily accessible location, such as concealed in a wrist band, attached to a keychain, or even in a credit card format (55). Eventually, the individual will experience a medical emergency (56). If, for example, an ambulance is called, then when the medical personnel arrive on scene, they will locate the portable device (57). The medical personnel will then be able to access the individual's medical information, entering a password if required (58). However, it is possible that when the individual experiences a medical emergency, the individual will go to an emergency room or other medical facility (59). The medical facility personnel will then be able to access the individual's medical information stored on the portable device, entering a password if required (60).

Medical information stored on the portable device can be updated by following the steps outlined in FIG. 2 and then following the steps outlined in FIG. 3.

Having described the present invention, it will now be apparent that many changes and modifications may be made to the above-described embodiments without departing from the spirit and the scope of the present invention.

The invention claimed is:

1. A method for transmitting personal health information from a databank to a health facility comprising the steps of:
 a) storing a person's health information in a databank, wherein said storing comprises the steps of:
  i) entering an individual's health information into said databank in a private file,
  ii) coding said private file with a unique identifying number or alpha-numeric sequence;
  iii) providing said individual with a barcode corresponding to said unique identifying number or alpha-numeric sequence;
 b) scanning said barcode with a scanner, wherein said scanning step comprises the steps of:
  i) using a scanner to scan said barcode;
  ii) transmitting to said databank said barcode's number or alpha-numeric sequence and a unique reference number or alpha-numeric sequence associated with said scanner;
  iii) matching said barcode's number or alpha-numeric sequence with said unique identifying number or alpha-numeric sequence at said databank;
  iv) authenticating said unique reference number or alpha-numeric sequence as an authorized user at said databank;
  v) transmitting said individual's health information to said scanner or other health facility further comprising the step of updating said health information by allowing said individual to enter and edit new health information via a website, further comprising the step of updating said health information with new form print-out by said individual comprising the steps of:
   a) viewing onscreen said information previously stored on said website;
   b) deciding which new form print-out to add to said website;
   c) printing a facsimile cover sheet with a unique confirmation number;
   d) electronically assigning said unique confirmation number to a blank file in said private file;
   e) faxing to a provided fax number said form print-out and said facsimile cover sheet;
   f) scanning into said database said form print-out and said facsimile cover sheet;
   g) associating said confirmation number on said facsimile cover sheet with said confirmation number in said private file;
   h) electronically placing said scanned print-out in said blank file in said private file and locking said blank file in said private file so said information will not be transmitted to a health facility until said blank file is unlocked;
   i) notifying said individual that said blank file in said private file is locked and awaiting approval;
   j) unlocking said blank file after said individual has viewed contents of said blank file over said website and approved said contents.

2. The method of claim 1 wherein said form printout includes a signature line for said individual's signature.

3. The method of claim 1 wherein said unique identifying number or alpha-numeric sequence is generated by a computer algorithm.

4. The method of claim 1 wherein said unique confirmation number or alpha-numeric sequence is generated by a computer algorithm.

5. The method of claim 1 wherein said scanner is a cellular telephone and said unique reference number or alpha-numeric sequence is a telephone number associated with said cellular telephone.

6. The method of claim 1 wherein said health facility is selected from the group consisting of a hospital, an ambulance or other emergency vehicle, a doctor's office, an emergency room, a nursing home, a convalescence home, an infirmary, a hospice or other health care facility.

7. The method of claim 1 wherein said barcode is constructed from at least one of the standardized barcode symbology libraries consisting of the group of UPC-A, UPC-E, ISBN, RSS-14, RSS-14E, RSS14L, Interleaved 2 of 5, EAN/JAN-8, EAN/JAN-13, Code 3, Code 39 Full ASCII, Code 128, PDF417, QR Code, and Data Matrix.

8. The method of claim 1 wherein said health information consists of at least one selected from the group consisting of medical history, surgical history, recent lab/test results, imaging studies, blood type, immunization history, medical device information, family history, social history, allergies, DNRs, genetic information, power(s) of attorney, living will, next-of-kin contact information, current medications, current supplements, current vitamins, drug tests, name and contact information for current physicians, choices of hospital, digital photograph, and advanced directive(s).

9. The method of claim 1 wherein said scanner is a PDA/cellular telephone and said unique reference number or alpha-numeric sequence is a telephone number associated with said PDA/cellular telephone, a MAC address, or a cell phones unique IME identifier.

10. The method of claim 1 further comprising the steps of accessing said health information in said databank with a computer, said computer being authenticated by matching Internet Protocol (IP) address of said computer with a list of authorized IP addresses.

11. The method of claim 1, further comprising the step of automatically contacting pre-approved list of contact people, said list being provided by said individual, when said unique reference number or alpha-numeric sequence of said authorized user is authenticated.

12. The method of claim 11 wherein said contacting is performed automatically by a uniquely created message, said message based upon details of situation and being vocalized using a voice synthesis engine with phone dialing capabilities.

13. The method of claim 11 wherein said contact people consists of at least one selected from the group of said individual's family members, said individual's friends, and said individual's next of kin.

14. The method of claim 1 further comprising the step of sending automated email to remind said individual to update said personal health information.

15. The method of claim 1, wherein said individual or said individual'a health care provider can scan or upload documents, including test results, over Hyper Text Transport Protocol Secure (https) directly into said databank.

16. The method of claim 1, wherein said individual or said individual's attorney can scan documents or upload, including advance directives, financial information, wills, legal contracts, mortgage satisfactions, or any other personal documents over Hyper Text Transport Protocol Secure (https) directly into said databank.

17. The method of claim 1, wherein said unique confirmation number or alpha-numeric sequence, said unique reference number or alpha-numeric sequence, and/or said unique identifying number or alpha-numeric sequence are generated by a computer algorithm, said computer algorithm comprising the steps of:
a) randomly selecting thirty-two letters and Arabic numerals to create a succession;
b) obtaining a GUID from operating system and adding it to said succession to create an array;
c) shifting said array bit-by-bit several times;
d) adding a hex number to said array to create a string;
e) adding a string to a second string to create a double string;
f) using the first twelve symbols of said double string as said unique confirmation number or alpha-numeric sequence, said unique reference number or alpha-numeric sequence, and/or said unique identifying number or alpha-numeric sequence.

18. The method of claim 1 wherein said personal health information can be stored in a portable device accessible by authorized personnel.

19. The method of claim 18 wherein a password is set by said individual to protect said personal health information that is stored on said portable device.

20. The method of claim 18 wherein said personal health information stored on said portable device is updated by connecting said device to the internet and downloading updates from said database.

21. The method of claim 18 wherein said device is one selected from the group consisting of a USB flash memory device, a memory card, and a credit card type device.

22. The method of claim 18 wherein said authorized personnel can access said stored personal health information via one selected from the group consisting of a desktop or laptop computer, an electronic personal organizer, and a cellular phone.

23. The method of claim 18 wherein said portable device is stored in one selected from the group consisting of a keychain, a wristband and a bracelet.

24. A method for transmitting personal health information from a databank to a health facility comprising the steps of:
a) storing a person's health information in a databank, wherein said storing comprises the steps of:
  i) entering an individual's health information into said databank in a private file,
  ii) coding said private file with a unique identifying number or alpha-numeric sequence;
  iii) providing said individual with an RFID corresponding to said unique identifying number or alpha-numeric sequence;
b) scanning said RFID with a scanner, wherein said scanning step comprises the steps of:
  i) using a scanner to scan said RFID;
  ii) transmitting to said databank said RFID and a unique reference number or alpha-numeric sequence associated with said scanner;
  iii) matching said RFID with said unique identifying number or alpha-numeric sequence at said databank;
  iv) authenticating said unique reference number or alpha-numeric sequence as an authorized user at said databank;
  v) transmitting said individual's health information to said scanner or other health facility further comprising the step of updating said health information by allowing said individual to enter and edit new health information via a website, further comprising the step of updating said health information with new form print-out by said individual comprising the steps of:
a) viewing onscreen said information previously stored on said website;
b) deciding which new form printout to add to said website;
c) printing a facsimile cover sheet with a unique confirmation number;
d) electronically assigning said unique confirmation number to a blank file in said private file;
e) faxing to a provided fax
f) scanning into said database said form print-out and said facsimile cover sheet;
g) associating said confirmation number on said facsimile cover sheet with said confirmation number in said private file;
h) electronically placing said scanned print-out in said blank file in said private file and locking said blank file in said private file so said information will not be transmitted to a health facility until said blank file is unlocked;
i) notifying said individual that said blank file in said private file is locked and awaiting approval;
j) unlocking said blank file after said individual has viewed contents of said blank file over said website and approved said contents.

* * * * *